United States Patent [19]

Taylor, Jr. et al.

[11] Patent Number: 5,583,266
[45] Date of Patent: Dec. 10, 1996

[54] INTEGRATED PROCESS FOR THE PRODUCTION OF ISOPROPYL ALCOHOL AND DIISOPROPYL ETHERS

[75] Inventors: Robert J. Taylor, Jr.; Pei-Shing E. Dai, both of Port Arthur; John F. Knifton, Austin, all of Tex.

[73] Assignee: Texaco Inc., White Plains, N.Y.

[21] Appl. No.: 236,807

[22] Filed: May 2, 1994

[51] Int. Cl.$^6$ ............................ C07C 41/00; C07C 29/14
[52] U.S. Cl. ............................................. 568/698; 568/881
[58] Field of Search ..................................... 568/698, 881

[56] References Cited

U.S. PATENT DOCUMENTS

| | | | |
|---|---|---|---|
| 4,704,482 | 11/1987 | Sanderson et al. | 568/922 |
| 5,011,506 | 4/1991 | Harandi et al. | 44/447 |
| 5,081,321 | 1/1992 | Fukuhara et al. | 568/881 |
| 5,304,601 | 4/1994 | Des Courieres et al. | 502/66 |
| 5,313,006 | 5/1994 | Knifton | 568/698 |
| 5,364,981 | 11/1994 | Knifton et al. | 568/698 |
| 5,430,198 | 7/1995 | Knifton et al. | 568/698 |
| 5,449,838 | 9/1995 | Knifton et al. | 568/698 |

*Primary Examiner*—José G. Dees
*Assistant Examiner*—Rosalynd A. Williams
*Attorney, Agent, or Firm*—James L. Bailey; Kenneth R. Priem; Cynthia L. Hunter

[57] ABSTRACT

A two-step integrated process for the generation of diisopropyl ether from a crude by-product acetone stream which comprises:

a) Hydrogenating said crude acetone over a supported, hydrogenation catalyst to give an isopropanol-rich effluent;

b) passing said isopropanol-rich intermediate directly to a second reactor, and c) subject said IPA to dehydration conditions in the presence of hydrogen and a strong acid zeolite catalyst from the group consisting of β-zeolite, optionally modified with one or more metals from Groups IB, VIB, VIIB and VIII of the Periodic Table, and a dealuminized Y-zeolite.

20 Claims, 3 Drawing Sheets

INTEGRATED PROCESS FOR THE PRODUCTION OF ISOPROPYL ALCOHOL AND DIISOPROPYL ETHERS

CROSS-REFERENCE

This application is related to U.S. Ser. Nos. 08/096,873; 08/057,373; and U.S. application Ser. No. 08/148,248, U.S. Pat. No. 5,364,981. It is also related to U.S. Pat. Nos. 4,822,921; 4,827,048; 5,099,072; 5,081,318; 5,059,725; 5,157,162; 5,162,592; 5,157,161; 5,183,947; 5,214,217; 5,214,218; and 5,220,078 all of which are incorporated by reference herein in their entirety.

FIELD OF THE INVENTION

This invention concerns an integrated two-step procedure for the production of high octane blending components for reformulated gasoline such as diisopropyl ether (DIPE), methyl t-butyl ether (MTBE) and isopropyl t-butyl ether (IPTBE), from a crude low value acetone stream containing acetone, methanol and t-butyl alcohol (tBA) which comprises (1) reducing the crude acetone stream in the presence of hydrogen over a reduction catalyst; and (2) feeding the reduced isopropanol directly into a second reactor where the IPA is converted to DIPE over an acidic catalyst. If MeOH or tBA are present in the feed, it is also possible to produce methyl tertiary butyl ether or isopropyl tertiary butyl ether, respectively.

DIPE and IPTBE, as well as MTBE, are useful as octane enhancers in gasoline.

BACKGROUND OF THE INVENTION

It is known to those skilled in the art that ethers, including both symmetrical and unsymmetrical ethers, may be prepared by reacting an alcohol with another alcohol to form the desired product. The reaction mixture, containing catalyst and/or condensing agent may be separated and further treated to permit attainment of the desired product. Such further treatment commonly includes one or more distillation operations.

Of the ethers which can be produced, a great deal of attention has been directed toward the production of methyl tertiary butyl ether (MTBE) for use as a gasoline oxygenate.

U.S. Pat. No. 4,918,244, to Nelson et al., discloses a method of preparing MTBE by continuously feeding t-butyl alcohol and methanol into a solid-acid catalyst bed, in a reactor separator rectification column in the presence of a solid acid catalyst, such as Amberlyst 15, whereby a product of substantially pure methyl tertiary butyl ether (MTBE) is separated from the reaction mixture.

An article titled "Expanding Refinery Technology leads to New Ether Potential," by William J. Peil, *Fuel Reformulation*, (1992, November/December) p. 34 contains a good review of the potential of ethers other than MTBE for use in meeting the EPA's requirements.

Though MTBE is the most widely produced and discussed ether, other ethers are also being evaluated, such as diisopropyl (DIPE) and ethyl tertiary butyl ether (ETBE). DIPE can be produced from refinery propylene and water with isopropanol as an intermediate in this process. In a variation, isopropyl tertiary butyl ether could be produced by combining isobutylene with isopropanol.

DIPE has similar physical and blending activities to MTBE and TAME and is a perfectly acceptable fuel oxygen source. Wood, A., *Chemical Week*, Apr. 15, 1992, p. 7.

The higher molecular weight ethers all have blending vapor pressures lower than MTBE, and much lower than ethanol. Their boiling temperatures are also higher than MTBE. Furthermore, higher molecular weight IPTBE has the potential to contribute more octane.

Although there has not been as much discussion regarding the production of IPTBE as there has been for MTBE, it is apparent that with its lower oxygen level and lower vapor pressure, there should be a definite niche for IPTBE in the future of reformulated gasoline.

The use of β-zeolites is known in the art for certain reactions.

The β-zeolite catalysts found useful in this integrated process for production of IPA, DIPE, MTBE and IPTBE have been known in the art for some time. One of the earliest disclosures of zeolite beta was in U.S. Pat. No. 3,308,069 (1967) to Wadinger et al.

J. B. Higgins, et al. of Mobil Research and Development published an article in *Zeolites*, 1988, Vol. 8, November, 446–452 titled "The Framework Topology of Zeolite Beta." In the article Higgins et al. disclose what is known about the framework topology of zeolite beta. The information has been determined using a combination of model building, distance-least-square refinement and powder pattern simulation.

In an article titled "Cumene Disproportionation over Zeolite β I. Comparison of Catalytic Performances and Reaction Mechanisms of Zeolites," *Applied Catalysis*, 77 (1991) 199–207, Tseng-Chang Tsai, Chin-Lan Ay and Ikai Wang disclose a study demonstrating that cumene disproportionation can be applied as a probe reaction for zeolite structure. It is revealed that zeolite beta would have application potential in the production of diisopropylbenzene for reasons of activity, selectivity and stability.

In a second part of the article, "II. Stability Enhancement with Silica Deposition and Steam Pretreatment", Ibid, pp. 209–222, Tsai and Wang disclose their development of two methods to improve the stability of zeolite beta, silica deposition and steam pretreatment.

Zeolites of low acidity can be achieved by a variety of techniques including steaming. In the case of steaming the zeolite can be exposed at elevated temperatures, 500° to 1200° F., preferably (750° to 1000° F.). This treatment is accomplished in 100% steam or an atmosphere of steam and gas which is substantially inert to the zeolite. A similar treatment can be accomplished at a lower temperature using elevated pressure, e.g., from about 350° F. to 700° F. with from about 10 to 200 ATM. Specific details of several steaming procedures can be gained from the disclosures of U.S. Pat. Nos. 4,325,994; 4,374,296 and 4,418,235.

Patents in the art which employ zeolite beta relate mainly to dewaxing, and cracking of hydrocarbon feedstock.

An article titled "Beta Zeolite as Catalyst or Catalyst Additive for the Production of Olefins During Cracking or Gas Oil," was written by L. Bonetto et al , 9th International Zeolite Conference, July 1992, FP 22. The authors note that with the greater demand for oxygenated compounds there is indication there might be increased demands for catalysts and conditions which maximize $C_3$, $C_4$ and $C_5$ olefins. They suggest that β-zeolite could be used alone or combined with Y-zeolite as a suitable zeolite component. Various catalysts were studied with respect to minimization of diffusional requirements and zeolite stability.

U.S. Pat. No. 4,419,220, to Mobil, discloses a process for dewaxing a hydrocarbon feedstock containing straight chain paraffins which comprises contacting the feedstock with a β-zeolite catalyst having a Si:Al ratio of at least 30:1 and a hydrogenation component under isomerization conditions.

Another European Application to Mobil, EP 0 094 82, discloses simultaneous catalytic hydrocracking and hydrodewaxing of hydrocarbon oils with β-zeolite.

In European Patent Application 0 095 303, to Mobil, there is a disclosure of dewaxing distillate fuel oils by the use of β-zeolite catalysts which, preferably have a silica:alumina ratio over 100:1. Ratios as high as 250:1 and 500:1 are disclosed as useful.

Another U.S. Pat. No. 4,518,485, to Mobil, discloses a process for dewaxing a hydrocarbon feedstock containing paraffins selected from the group of normal paraffins and slightly branched paraffins and sulfur and nitrogen compounds where, after conventionally hydrotreating the feedstock to remove sulfur and nitrogen, the hydrotreated feedstock is dewaxed by contacting the feedstock with a catalyst comprising a β-zeolite having a silica/alumina ratio of at least 30:1.

In U.S. Pat. No. 4,740,292, to Mobil, there is disclosed a catalytic cracking process which comprises cracking a hydrocarbon feed in the absence of added hydrogen with a cracking catalyst comprising a β-zeolite component and a faujasite component comprising at least one crystalline aluminosilicate of the faujasite structure, the weight ratio of the faujasite component to the β-zeolite component being from 1:25 to 20:1.

Large pore β-zeolite has been employed in the synthesis of industrially important para-cumene by toluene isopropylation. See "Toluene Isopropylation over Zeolite β and Metallosilicates of MFI Structure," P. A. Parikh et al., *Applied Catalysis, A*, 1992, 90, p. 1.

In European Patent 323 138 and U.S. Pat. No. 4,906,787, there is disclosed a catalytic process for converting light olefins to ethers suitable as high octane blending stocks carried out by contacting the olefin, especially propene, with water and alcohol recovered from a downstream distillation operation in an olefin conversion unit in the presence of an acidic zeolite catalyst. In this work diisopropyl ether (DIPE) was prepared from $C_3H_6$ and aqueous iso-PrOH in the presence of silica-bound zeolite Beta catalyst at 166°.

In U.S. Pat. No. 5,144,086, to Harandi et al., there is disclosed an integrated multistage process for the production of diisopropyl ether from substantially pure propene wherein in the second stage isopropanol containing about 0–20% water is contacted with an acidic large pore zeolite etherification catalyst which comprises a β-zeolite having a silica to alumina ratio of about 30:1 to 50:1.

In a European Patent, EP 323 268, light olefins are converted to alcohols and/or ethers in the presence of β-zeolite.

U.S. Pat. No. 4,058,576 to Chang et al. teaches the use of (pentasil-type) aluminosilicate zeolites, such as ZSM-5, having a pore size greater than 5 angstrom units and a silica-to-alumina ratio of at least 12, to convert lower alcohols to a mixture of ethers and olefins.

U.S. Pat. No. 4,714,787, to Bell etal., discloses a process for the manufacture of methyl isopropyl ether from methanol and a $C_3$ hydrocarbon fraction that contains 20 to 100 wt. % of propylene, which process comprises preparing a mixture of said hydrocarbon fraction and 0.1 to 10 mole of methanol per mol of propylene contained in said fraction, contacting said mixture with a solid insoluble acid catalyst comprising materials having the structure of zeolite Beta, said contacting being effected under a combination of conditions effective to selectivily form said ether.

U.S. Pat. No. 5,225,609 to Bell discloses a process for the production of alkyl tertiary alkyl ether employing a zeolite catalyst, particularly zeolite beta which is pretreated either by steaming or hydrothermal treatment using liquid water at elevated temperatures. This process is claimed to be particularly effective in reducing the formation of dimer by product in the zeolite Beta catalyzed process for the formation of methyl tertiary butyl ether (MTBE) with high selectivity.

The use of faujasite zeolites in alkyl ether formation is also known in the art. The following references discuss the use of faujasite zeolites in various applications.

Japanese Patent 82-07432 teaches the use of zeolites, particularly mordenites and faujasites, to make dialkyl ethers containing primary or secondary alkyl groups by the liquid phase dehydration of alcohols.

In allowed U.S. Pat. No. 5,214,217, to Texaco Chemical Company, there is disclosed a method for preparing methyl tertiary butyl ether by reacting butanol and methanol in the presence of a catalyst comprising a super-acid alumina or a faujasite-type zeolite.

In U.S. Pat. No. 5,081,318, a Y-type zeolite modified with fluorosulfonic acid is disclosed.

In U.S. Pat. No. 3,955,939, to Sommer et al. (1976), there is disclosed the production of a water-free mixture of isopropyl alcohol, diisopropyl alcohol, diisopropyl ether and by-products by the catalytic hydration of propylene in the gaseous phase at temperatures of 140°–170° C. in the presence of a catalyst comprising a super-acid alumina or a faujasite-type zeolite.

It is also known to produce IPA and DIPE by the hydration of propylene and subsequent dehydration of IPA to DIPE.

In U.S. Pat. No. 5,208,387, also to Harandi et al., there is disclosed a process for the acid catalyzed production of DIPE from propene and water feed stream that eliminates the propene recycle stream to the olefin hydration reactor and achieves high propene conversion. This process is carried out in two stages wherein the first stage comprises a zeolite catalyzed hydration and etherification of propene employing a minimum of water feed and the second stage converts unconverted propene from the first stage reactor by hydration and etherification to DIPE.

In an article titled "Race to License New MTBE and TAME Routes Heats Up", Rotman, D., *Chemical Week*, Jan. 6, 1993, p. 48, there is a review of new technology at several different companies which centers around skeletal isomerization, particularly of $C_4$ and $C_5$ olefins. The interest in this technology is fueled by the promise of dramatically increased and relatively inexpensive isobutylene and isoamylene that could boost MTBE and TAME production, often constrained by the amounts of available isobutylene in refinery or steam cracker streams. DIPE production from propylene is also discussed.

Mobil Corp. has disclosed new etherification technology that can produce fuel oxygenates based only on olefinic refinery streams and water. This process has the potential to allow refiners to produce oxygenates without having to rely on an external supply of alcohols. The technology is developed around diisopropyl ether (DIPE) based on propylene. Wood, A., supra, p. 7.

In related copending Ser. No. 08/175,450, U.S. Pat. No. 5,449,838, there is disclosed a two-step process for generation of isopropyl t-butyl ether from crude acetone.

In related copending Ser. No. 08/148,244, U.S. Pat. No. 5,430,198 there is disclosed a two-step process for the generation of diisopropyl ether from a crude by-product acetone stream which comprises hydrogenating said crude acetone over a bulk metal, nickel-rich catalyst to give an isopropanol effluent and subjecting said isopropanol-rich intermediate to dehydration conditions in the presence of a strong acid zeolite catalyst. This process requires interstage separation of the hydrogen prior to the dehydration step.

It does not appear that there is any disclosure or suggestion in the art of converting acetone to ethers in an integrated process. The portion of said by-product stream which typically comprises acetone is about 20% to 80%. The by-product acetone stream may also contain greater than 5% of both methanol (MeOH) and t-butanol (tBA). It would greatly enhance the economics of any process to produce MTBE or other oxygenates if acetone, along with some methanol and t-butanol, from a by-product stream could be converted to oxygenates such as DIPE, IPTBE and MTBE.

SUMMARY OF THE INVENTION

In accordance with the foregoing the novel method of the instant invention for generation of diisopropyl ether, isopropyl tertiary butyl ether and methyl tertiary butyl ether from a crude by-product stream is an integrated process which comprises:

(1) reducing the crude acetone stream, which may also contain methanol and t-butanol, in the presence of hydrogen and a reduction catalyst, and (2) feeding the reduced isopropanol directly into a second reactor and reacting it over a series of strong acid zeolite catalysts from the group consisting of β-zeolite, dealuminized Y-zeolites, and metal-modified β-zeolite, optionally in combination with an oxide of Group III or IV.

DETAILED DESCRIPTION OF THE INVENTION

Figure 1:
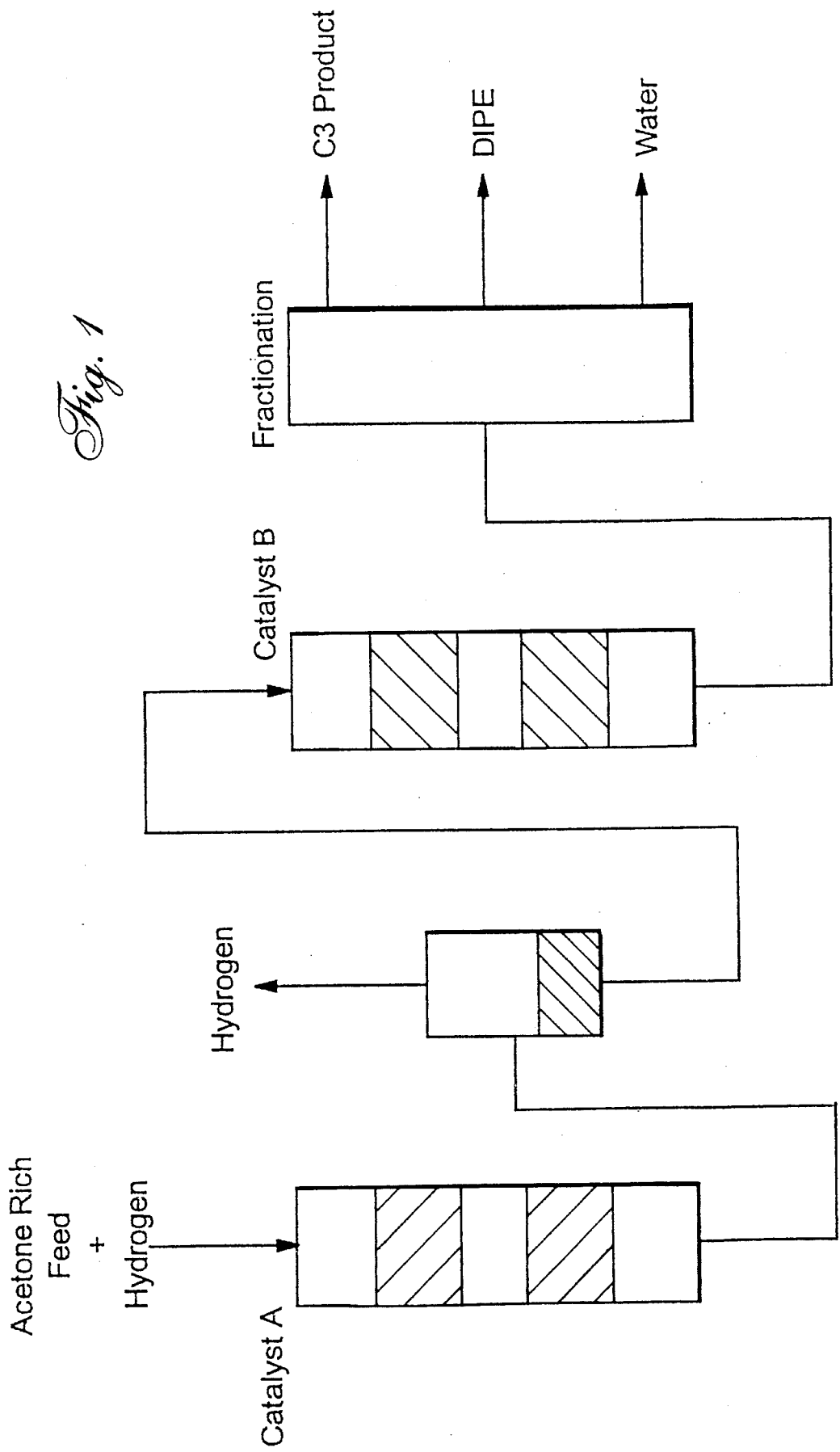
FIG. 1 is a drawing of a process in the art for producing DIPE which requires interstage separation.
Figure 2:
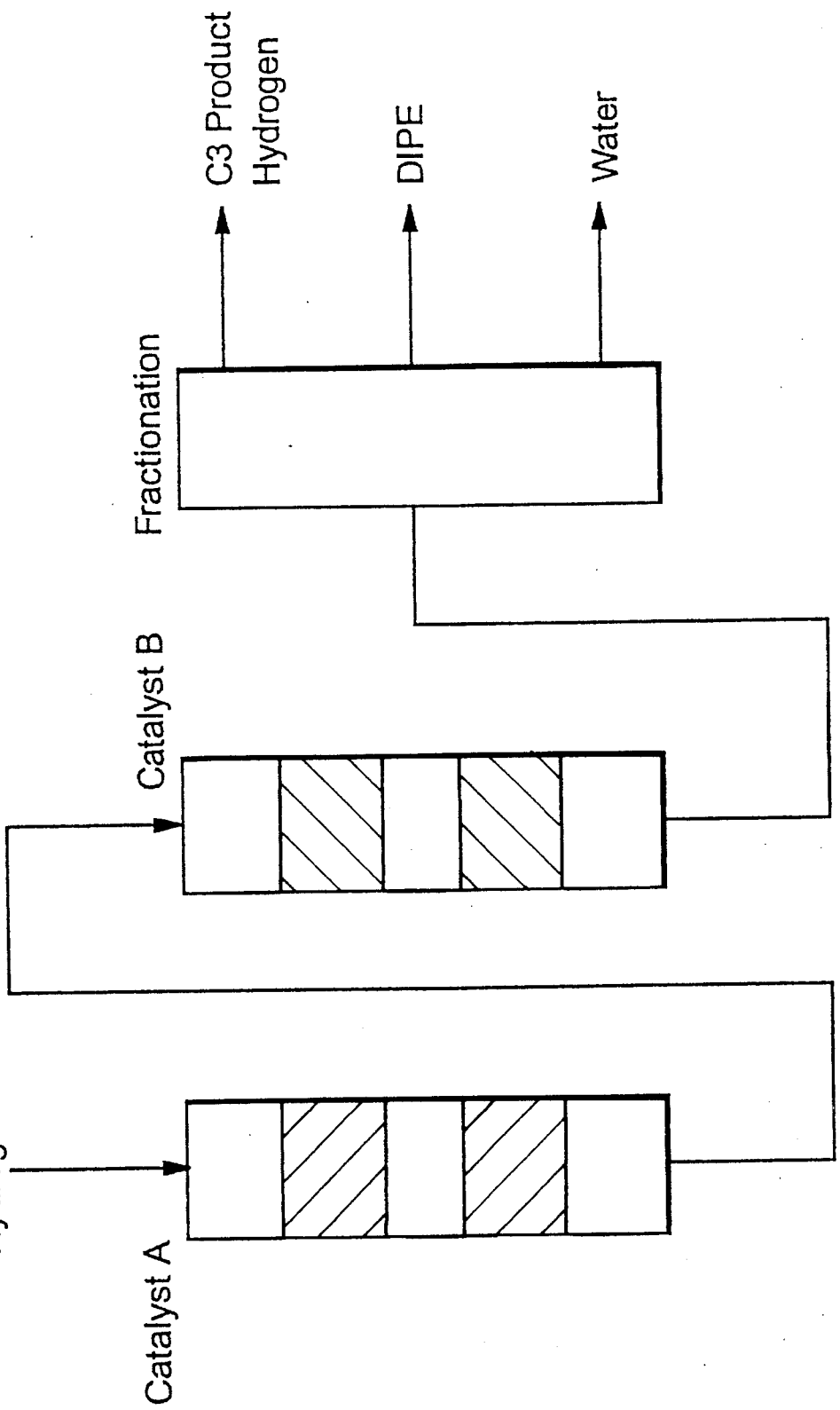
FIG. 2 is a drawing of an integrated process for producing DIPE from acetone without interstage separation.
Figure 3:
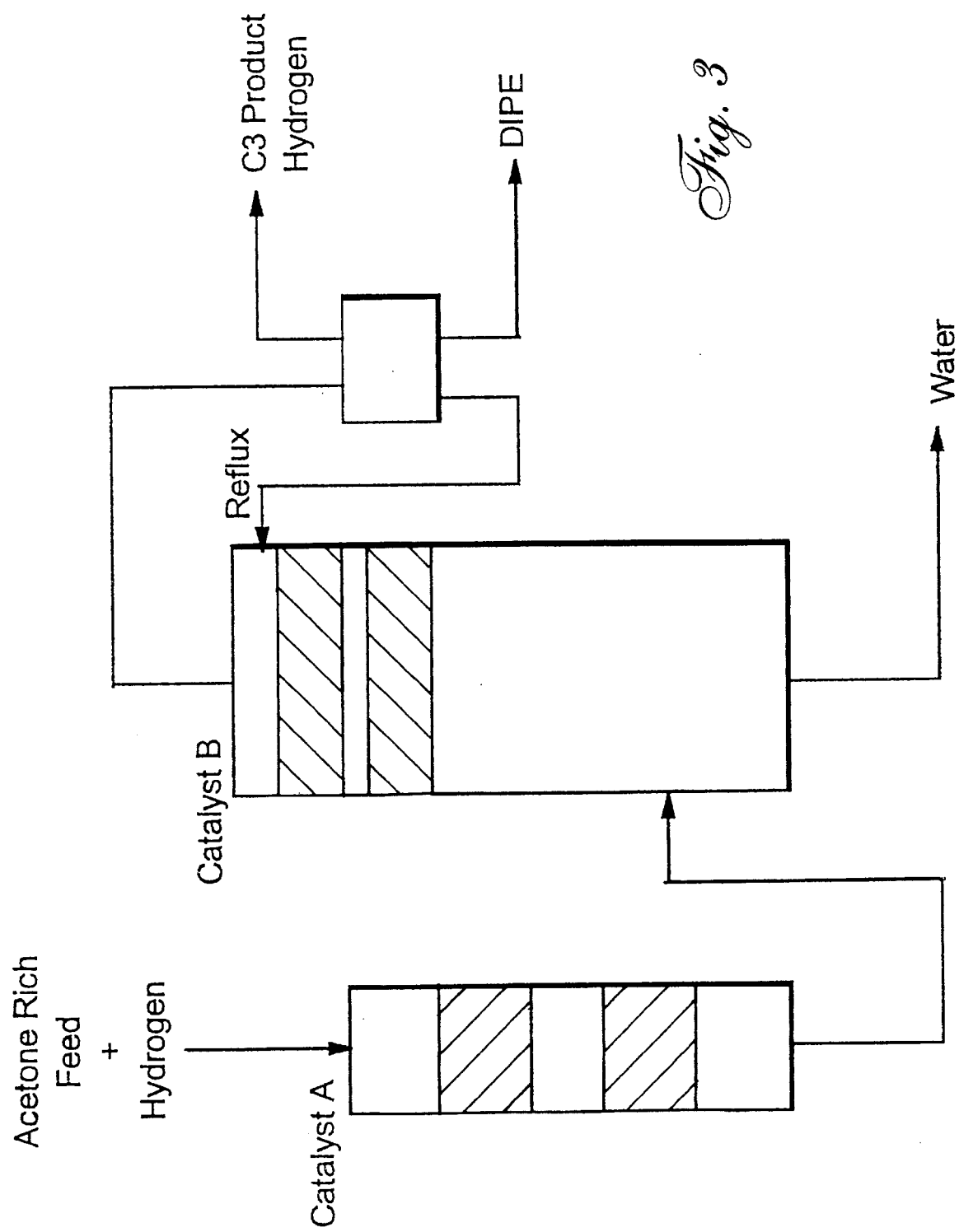
FIG. 3 is a drawing of an integrated process for providing DIPE from acetone which uses catalytic distillation for the etherification portion of the process.

In a process to make propylene oxide a large number of by-products are typically generated with the desired product. The by-products may include formic acid, acetic acid, their ester derivatives, t-butanol and acetone. The acetone may constitute about 20% to 80% of certain crude by-product streams. These crude acetone streams may be further mixed with methanol.

Copending Ser. No. 08/148,244, U.S. Pat. No. 5,430,198 discloses a two-step process for generation of DIPE which requires interstage separation of hydrogen. Removal of hydrogen can cause propylene to oligomerize in the etherification reactor. In a commercial process this can greatly increase costs for purification of the DIPE product and regeneration of the catalyst.

The instant invention provides an integrated process for the production of isopropyl alcohol and diisopropyl ether (DIPE), as well as methyl tertiary butyl ether (MTBE) and isopropyl tertiary butyl ether (IPTBE) where the crude acetone stream also contains methanol and t-butyl alcohol. For the generation of each of these oxygenates respectively the crude acetone should contain 10–40% each of methanol and t-butanol.

The integrated synthesis can be represented by:

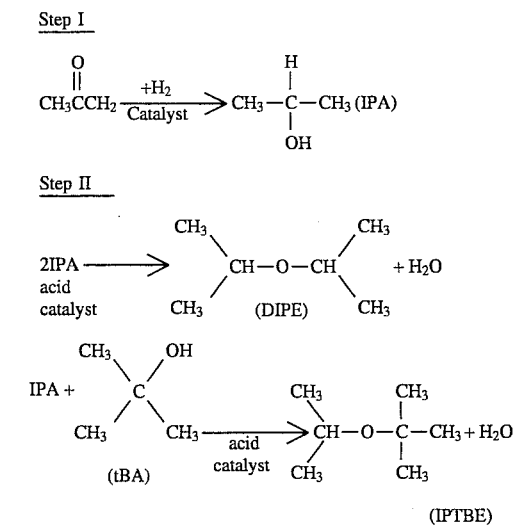

In the first step the crude acetone stream is passed over a nickel-rich catalyst. The total metals loading of the catalyst is the range of 28 to 40 wt % of the support. The support material could be either one of the alumina, zirconia-alumina, titania-alumina and zeolite-alumina. The support comprises greater than 80% alumina and less than 20% of the other metal oxides. The preferred support for the catalyst used in the first step is alumina. A preferred nickel catalyst is characterized by having the composition, calculated in mol %, of from about 60%–85% nickel, and 1%–30% copper with the preferred proportions being about 65%–88% nickel, and 12%–35% copper The temperature necessary to achieve the desired acetone hydrogenation to isopropanol (IPA) is 50°–200° C., the preferred range is 100°–150° C.

The conversion of acetone to isopropanol in the first step is normally >90% per pass in continuous processing and in some instances it is as great as 99% or more.

In contrast to previous disclosures where a fractionation step is required after the hydrogenation of the acetone, the instant invention provides an improvement in that the alcohol-rich effluent from the first reactor goes directly to a second reactor without separation of the liquid and gas.

In addition to saving the cost of fractionation, a potential benefit is the complete removal of any peroxides such as di-t-butyl peroxide present in the crude acetone stream, which is a poison to acidic catalysts.

In the second reactor the alcohols can be etherified to ethers over an acidic catalyst, such as, for example, β-zeolite, ZSM-5, or Y-zeolite in the presence of hydrogen. The ether-rich effluent can subsequently be fractionated to isolate the ethers, such as, for example, DIPE, MTBE, and IPTBE for use as octane enhancers.

The zeolite can optionally be impregnated with a Group IB or VIII metal, including, but not limited to nickel and copper. This is demonstrated in Examples 1 and 2. In another embodiment, the metals can be deposited on a zeolite in combination with an oxide of Group III or IV of the Periodic Table. This is demonstrated in Examples 3 and 4.

The composition of zeolite beta is described in U.S. Pat. Nos. 3,308,069; 4,419,220; 4,518,485 and 4,740,292. In those references, zeolite beta is typically described as follows:

Zeolite beta is a crystalline aluminosilicate having a pore size greater than 5 Angstroms. The composition of the zeolite, as described in U.S. Pat. No. 3,308,069, in its as synthesized form may be expressed as follows:

$$[XNa(1.0\pm0.1-X)TEA]AlO_2.YSiO_2.WH_2O$$

where X is less than 1, preferably less than 0.7; TEA represents the tetraethylammonium ion; Y is greater than 5 but less than 100; and W is up to about 60 (it has been found that the degree of hydration may be higher than originally determined, where W was defined as being up to 4), depending on the degree of hydration and the metal cation present. The TEA component is calculated by differences from the analyzed value of sodium and the theoretical cation to structural aluminum ratio of unity.

As discussed in the J. B. Higgins, et al. reference, Supra, p. 446, the first clues to the crystal structure of zeolite beta were evidenced from chemical and physical property measurements. Ion-exchange isotherms of Na-β at 25° C. indicated that cations as large as tetraethylammonium (TEA$^+$) exchanged completely into the pore system. This behavior suggests that beta contains at least 12-membered rings opening into channels, because TEA$^+$ is too large to exchange through 10-membered rings such as those in ZSM-5. The complete exchange of cations in beta indicated the presence of channels instead of cages, because it is not possible to remove all the cations from cage structures such as Na faujasite. Additional evidence was obtained from organic sorption data and density measurements. Cyclohexane sorption of 14.6–19.4 wt % and a measured density of 1.61 g/cm$^3$ ruled out undimensional pore systems such as those in ZSM-12, ZSM-22, ZSM-23 and ZSM-48. Structural similarities among beta, mordenite and ZSM-12 were suspected because all three may be synthesized in Na$^+$-TEA$^+$ systems from highly siliceous batch compositions. Further, zeolite beta is easily synthesized in the SiO$_2$/Al$_2$O$_3$ range of 30–50. This lies between TEA$^+$ mordenite (typically 10–30) and ZSM-12 (typically, >60), suggesting the beta framework contains large fractions of both 4- and 5-membered rings.

In the Tsai and Wang reference, Supra, part II, p. 209, stability enhancement is discussed. Two methods, silica deposition and steam pretreatment, have been developed to substantially improve zeolite beta stability.

Ibid, p. 215, it is stated that zeolite beta has two types of three dimensional pore openings, the linear and the tortuous channel. The former has pore openings of 7.5 Å×5.7 Å and the latter has pore openings of 6.5 Å×5.6 Å. When silica, for example, is deposited on zeolite beta, the pore opening was narrowed or blocked by the deposited silica. It was concluded that silica deposition selectively removes strong acid sites and increases the population of medium acid sites.

In the fully base-exchanged form, zeolite beta has the composition:

$$[(X/n)M(1\pm0.1-X)H]AlO_2.YSiO_2.WH_2O$$

where X, Y and W have the values listed above and n is the valence of the metal M. This form of the zeolite may be converted partly to the hydrogen form by calcination, e.g. at 200° C. to 900° C. or higher. The completely hydrogen form may be made by ammonium exchange followed by calcination in air or an inert atmosphere such as nitrogen, see U.S. Pat. No. 4,419,220.

Zeolite beta is characterized by the following X-ray diffraction pattern:

d Values of Reflection in zeolite beta
11.40±0.2
7.40±0.2
6.70±0.2
4.25±0.1
3.97±0.1
3.00±0.1
2.20±0.1

The preferred forms of zeolite beta are the highly acidic, high silica forms, having silica-to-alumina mole ratio of at least 10:1, and preferably in the range of 10:1 to 50:1 in the as-synthesized form, and a surface area of at least 100 m$^2$/g.

Suitable β-zeolites for the practice of this invention include Valfor C806β, Valfor CP815β and Valfor C861. Valfor® is the registered trademark of the PQ Corporation. Valfor® C806β zeolite is zeolite beta powder in template cation form. It is a high silica shape selective zeolite which contains the organic template used in the crystallization step, having been isolated after filtration and washing of the synthesis product. C806β has a SiO$_2$/Al$_2$O$_3$ molar ratio of 23–26; the crystal size is 0.1–0.7 um; the surface area after calcination is about 700–750 m$^2$/g; the cyclohexane adsorption capacity after calcination is 19–24 g/100 g; Na$_2$O content is about 0.01–1.0% by weight anhydrous; and, the organic content is about 11–13% by weight, on a water-free basis.

Valfor® C815β zeolite is a calcined zeolite beta powder in hydrogen, sodium form. It is similar to C806β except the product has been calcined to decompose the organic template. C815β is a high silica, shape selective aluminosilicate with a large pore diameter. C815β also has a SiO$_2$/Al$_2$O$_3$ molar ratio of about 23–26; the crystal size, surface area, cyclohexane adsorption capacity and Na$_2$O are all within the same ranges as given for C806β.

Valfor® C861β is an extrudate made of 80% C815β powder and 20% alumina powder.

Y-zeolites are also useful and are from the group of faujasite zeolites. The unit cells of faujasite zeolites are cubic, a$_o$≈2.5 nm, and each contains 192 silicon- or aluminum-centered oxygen tetrahedra which are linked through shared oxygen atoms. Because of the net negative charge on each of the aluminum-centered tetrahedra, each unit cell contains an equivalent number of charge-balancing cations. These are exclusively sodium ions in zeolites in their synthesized form. Typical cell contents for the Y-zeolites in the hydrated form are:

$$Na_{56}[(AlO_2)_{56}(SiO_2)_{136}]_x \cdot 250\ H_2O$$

Y-zeolites are distinguished on the basis of the relative concentration of silicon and aluminum atoms and the consequent effects on detailed structure and related chemical and physical properties. The aluminum atoms in the unit cell of Y-zeolite vary from 76 to 48, resulting in a Si:Al ratio between 1.5 and 3.0. Both the cation concentration and charge density on the aluminosilicate structure are lower for Y-zeolites than for X-zeolites, where the aluminum atoms in the unit cell vary from 96 to 77.

The feature which determines the difference between faujasites and other zeolites built up from sodalite units is the double 6-membered ring or hexagonal prism, by which the units are linked. The sodalite unit, or β-cage, can be represented by a truncated octahedron, with the 24 silicon or aluminum atoms(designated T atoms) taking positions at the vertices. The 36 oxygen atoms are displaced from the midpoints of the edges joining the vertices in order to attain tetrahedral configuration around the T atoms. The free diameter of the void within the β-cage is 0.66 nm, but only the smallest molecules can enter through the 0.22 nm diameter opening in the distorted ring of six oxygen atoms associated with each hexagonal face. Each sodalite unit is linked tetrahedrally across hexagonal faces by six bridging oxygens to four other sodalite units. The larger void spaces enclosed by sodalite units and hexagonal prisms are termed α-cages, or supercages. The α-cage is a 26-hedron with a free diameter of ≈1.3 nm, and it can be entered through four distorted 12-member rings of diameter 0.80–0.90 nm. In this way each α-cage is tetrahedrally joined to four others giving a complex system of void space extending throughout the zeolite structure. The α- and β-cages together give Y-zeolites, along with X-zeolites, the largest void volume of any known zeolites, which is ca. 50 vol % of the dehydrated crystal. From the catalytic viewpoint, the α-cages are by far the most important, since, unlike the β-cages, they permit entry of numerous aliphatic and aromatic compounds.

As demonstrated in related, copending U.S. application Ser. No. 08/148,244, U.S. Pat. No. 5,430,198 filed Nov. 8, 1993, these Y-zeolites are particularly effective in the dealuminated form. Preferably, said Y-zeolites are dealuminated by ammonium exchange followed by calcination, or by treatment with ethylenediaminetetraacetic acid (EDTA) or other chelating agents or by treatment with fluorine or a fluorine-containing compound such as silicon tetrafluoride or ammonium fluorosilicate, or hydrothermal treatment and/ or acid treatment. Said dealuminated Y-zeolites should have a silica-to-alumina molar ratio of greater than three, preferably a ratio of 5 or greater and most preferably a silica-to-alumina ratio of 5 to 100. The examples demonstrate the usefulness of catalysts having a silica-to-alumina ratio of 5 to 25 and particularly 5 to 10.

Examples of suitable commercially available dealuminized Y-zeolites include UOP's LZY-82 and LZY-72, PQ Corporation's CP-304-37 and CP-316-26, UOP's Y-85, Y-84, LZ-10 and LZ-210.

The unit cell size and $SiO_2/Al_2O_3$ molar ratio for typical dealuminated Y-zeolites are noted in the following table:

| ZEOLITE TYPE | UNIT CELL SIZE, A | $SiO_2/Al_2O_3$ MOLAR |
|---|---|---|
| LZY-82 | 24.53 | 7.8 |
| LZY-85 | 24.49 | 9.1 |
| LZY-10 | 24.32 | 23.7 |
| LZY-20 | 24.35 | 18.9 |
| LZY-84 | 24.51 | 8.4 |
| LZ-210 | 24.47 | 9.9 |
| LZY-72 | 24.52 | 8.1 |
| CP316-26 | 24.26 | 45.7 |

Said catalysts may be formed in the presence of a binder, such as Group III or Group IV oxide. Group IV oxides used in conjunction with said β-zeolite include oxides of aluminum, silicon, and titanium, zirconium, as well as combinations thereof. Alumina is preferred. Said binders may comprise 10% to 90% of the formed catalyst.

Particularly effective in the subject integrated production of DIPE, MTBE and IPTBE are the β-zeolites, optionally bound to an oxide, modified with multiple metals.

The metals useful for modifying the zeolite in the instant invention comprise those from Groups IB and VIII of the Periodic Table. Preferred metals are those found in Groups IB and VIII of the Periodic Table and include copper, nickel, palladium and platinum. Especially good results were observed using combinations of nickel and copper on a β-zeolite in combination with alumina.

Said zeolites are preferably impregnated with said specified metals as their salts, particularly their metal nitrate or chloride salts, in an aqueous, alcoholic, or ketonic media over a period of 1–24 hours, then the solids are dried at elevated temperature, e.g. 120° C., for a period of time and calcined at 300°–800° C. for a further period, e.g. 315° C. for 2 hours, followed by 540° C. for another 2 hours, then reduced in a stream of hydrogen at ≧200° C.

The amount of the various metals deposited on the zeolite can vary. The amount of each individual metal, i.e., copper, nickel, palladium and platinum can vary from 0.01 to 10.0%. Where copper and nickel are deposited on zeolite/alumina extrudates the preferred weight percent is from 0.1% to 5.0%.

Said catalysts may be in the form of powders, pellets, granules, spheres, shapes and extrudates. The examples described herein demonstrate the usage of granules.

The process of the instant invention is carried out in two reactors in a series. The hydrogenation reaction of crude acetone stream is performed in a liquid phase downflow or upflow fixed bed reactor. The hydrogenation catalyst could be packed (loaded) into one, or more than one, zone with a quench zone in between the catalyst zones. The heat evolved from the hydrogenation reaction could be effectively removed by the quench stream in order to better control the reactor temperature. The etherification reaction could be conducted in either a fixed bed reactor or a catalytic distillation column.

Dehydration to the oxygenates can generally be conducted at temperatures from 20° to 250° C.; the preferred range is 80° to 200° C. Good results are observed throughout this temperature range. However, it can be noted that the best conversion figures for MTBE, DIPE and IPTBE cogeneration are observed when the temperature is 120°–180° C. The total operating pressure may be from 0 to 2000 psig, or higher. The preferred pressure range is 100 to 1000 psi.

Typically, DIPE is generated continuously in up to ca. 30 wt % concentration or greater in the crude liquid product at total liquid hourly space velocities (LHSV) of 0.1–10/hour and relatively mild conditions, where:

$$LHSV = \frac{\text{Volume Of Total Liquid Feed Run Into The Reactor Per Hour}}{\text{Volume of Catalyst In Reactor}}$$

It is anticipated that MTBE and IPTBE can be generated in up to 20 or 15 wt % concentration or greater, respectively.

Conversions of isopropanol (IPA) are estimated in the following examples using the equation:

$$\frac{(\text{Mole \% of } IPA \text{ in Feed} - \text{Mole \% of } IPA \text{ in Product})}{\text{Mole \% of } IPA \text{ in Feed}} \times 100$$

The examples which follow illustrate the integrated process for the synthesis of DIPE, and optionally IPTBE and MTBE, from a pure acetone feed, and optionally a crude acetone stream containing Acetone, TBA, MeOH, using β-zeolites, optionally modified with multiple metals, wherein the β-zeolites are optionally bound with an oxide.

The accompanying examples specifically demonstrate:

Although 35.8 wt % DIPE is obtained in Example 7, run 6013-700 using 32% Ni/Cu on $Al_2/O_3$ in the top bed and 32% 60/40 Beta/$Al_2O_3$ in the bottom bed, there is also 9.2 wt % gas produced.

The overall best results might be typified by Example 5, Cut No. 6012-700 using the same top bed catalyst with 32% Ni/Cu on 80/20 Beta/$Al_2O_3$ on the bottom. Here the wt % of DIPE is 30.0, however the wt % of undesirable gas is reduced to 4.6.

Catalyst Evaluation Procedure

Catalyst screening runs were performed in a microreactor test unit which has two reactors in series separated by a quench zone. The reactors were operated in a downflow configuration. The top reactor was loaded with a 4 cc catalyst. The second reactor has two catalyst beds of 4 cc of catalyst each separated by a 4 cc bed of inert material. The total charge of catalyst was 12 cc in the unit. Internal thermocouples were positioned at the bottom of each catalyst bed and at the inlet to the first reactor. The liquid feed was charged to the unit using a high pressure pump and the hydrogen was metered through a mass flow controller. For the purpose of simplifying the analysis of liquid products by GC, pure acetone (technical grade, 97%) was used as a feedstock to demonstrate the chemistry involved in the instant invention.

The catalysts were activated by heating slowly from room temperature to 500° F. over a 6 hour period under flowing nitrogen at 70 psig. The unit pressure was then raised to 500 psig with hydrogen and the catalyst bed was held at 500° F. for 10 hours under flowing hydrogen. The catalyst bed was cooled down to below 200° F. The acetone feed was charged to the unit at 1 LHSV based on total catalyst volume. The hydrogen flow rate can range from 1:1–10:1, however it was controlled to give a hydrogen to acetone mole ratio of 5:1 and a total pressure of 500 psig. The acetone feed was mixed with hydrogen and preheated to 220° F. It was then fed into the first reactor which contained the hydrogenation catalyst. The first reactor was operated adiabatically. The hydrogenated feed left the first reactor and entered the second reactor. The reaction temperature in the second reactor was varied from 240° F. to 300° F. The liquid product was collected periodically in a chilled receiver at 0° F. and 300 psig. The product was analyzed by GC to determine the composition of hydrocarbon and oxygenates, and by Karl-Fischer titration for the water content.

PREPARATION OF CATALYSTS

EXAMPLE 1

A 92 gram batch of alumina support was impregnated with a 68 cc aqueous solution containing 94 g of nickel nitrate hexahydrate and 9.9 gram of copper nitrate hemipentahydrate. The impregnated support was dried at 250° F. for 16 hours, and then calcined at 600° F./4 hours. The calcined support was impregnated again with a 68 cc aqueous solution containing 94 g of nickel nitrate hexahydrate and 9.9 g of copper nitrate hemipentahydrate. The impregnated support was dried at 250° F. for 16 hours, and then calcined at 600° F. for 4 hours and 900° F. for 8 hours. The finished catalyst is Example 1.

EXAMPLE 2

A 50 g batch of 80% β-zeolite/20% alumina support was impregnated with a 41 cc aqueous solution containing 51 g of nickel nitrate hexahydrate and 5.4 g of copper nitrate hemipentahydrate. The impregnated support was dried at 250° F./2 hours, and then calcined at 600° F./4 hours. The calcined support was impregnated again with a 38 cc aqueous solution containing 51 g of nickel nitrate hexahydrate and 5.4 g of copper nitrate hemipentahydrate. The impregnated support was dried at 250° F./2 hours, and then calcined at 900° F./8 hours. The finished catalyst is Example 2.

EXAMPLE 3

A 100 g batch of 30% β-zeolite/70% alumina support was impregnated with a 80 cc aqueous solution containing 102 g of nickel nitrate hexahydrate and 10.8 g of copper nitrate hemipentahydrate. The impregnated support was dried at 250° F./2 hours, and then calcined at 600° F./4 hours. The calcined support was impregnated again with a 73 cc aqueous solution containing 102 g of nickel nitrate hexahydrate and 10.8 g of copper nitrate hemipentahydrate. The impregnated support was dried at 250° F./2 hours, and then calcined at 900° F./8 hours. The finished catalyst is Example 3.

EXAMPLE 4

A 1011 g batch of Catapal B alumina powder was mixed with 3989 g β-zeolite powder to make a 60/40 wt % mix based on dry powders. An aqueous solution containing 9.17 g conc. nitric acid and 2128 g water was prepared and added to the alumina/zeolite mix. An additional 214 g of water was added. The paste was mix/mulled then extruded to normal $\frac{1}{16}$-inch extrudates using a 2-inch screw extruder. The extrudates were dried at 110° C. overnight.

EXAMPLE 5

Example 5 is an example of the invention. The catalyst from Example 1 was loaded in the top reactor and the catalyst from Example 2 was loaded in the bottom reactor. The Catalyst Evaluation Procedure described above was used. The results for this example are given in Table I. Under the test conditions, almost complete conversion of acetone was achieved. IPA and DIPE are cogenerated as the desired reaction products with high yields. Very small amounts of undesired propylene products are formed by the dehydration reaction of IPA. The DIPE yields increase with increasing temperatures of the etherification reactor (bottom reactor).

TABLE I

| | | | | Results of Catalyst Evaluations | | | | | |
|---|---|---|---|---|---|---|---|---|---|
| | | Example 5: | Top Bed | - 32% Ni/Cu on Al2O3 | | | | | |
| | | | Bot. Bed | - 32% Ni/Cu on 80/20 Beta/Al2O3 | | | | | |
| | | | | GC Analysis of Liquid Product | | | | | |
| Cut No. | TOS hr. | Avg. Top Temp. °F. | Avg. Bot. Temp. °F. | Liq. Recov. wt % | C3 wt % | Acetone wt % | IPA wt % | DIPE wt % | Water wt % | Gas wt % |
| 6012-600 | 9 | 239 | 258 | 98.6 | 0.3 | 0.6 | 83.9 | 8.7 | 4.8 | 1.4 |
| 6012-700 | 20 | 244 | 278 | 95.4 | 0.5 | 0.5 | 54.3 | 30.0 | 10.0 | 4.6 |

EXAMPLE 6

Example 6 is an example of the invention. The catalyst from Example 1 was loaded in the top reactor and the catalyst from Example 3 was loaded in the bottom reactor. The Catalyst Evaluation Procedure described above was used. The results for this example are given in Table II. This example is used to illustrate the effect of β-zeolite content or catalyst acidity on the DIPE yield. Example 6 appears to exhibit a small advantage in DIPE yield over Example 5 at lower etherification reactor temperature, however, at higher temperature it does not give any advantage. As the space velocity was raised from 1 to 2 while maintaining the etherification reactor constant temperature, IPA yield increased and DIPE yield decreased. The results imply that Example 6 does not have sufficient acidic sites to convert the IPA to DIPE at the higher space velocity.

TABLE II

Results of Catalyst Evaluations

Example 5: Top Bed - 32% Ni/Cu on Al2O3
Bot. Bed - 32% Ni/Cu on 80/20 Beta/Al2O3

GC Analysis of Liquid Product

| Cut No. | TOS hr. | Avg. Top Temp. °F. | Avg. Bot. Temp. °F. | Liq. Recov. wt % | C3 wt % | Acetone wt % | IPA wt % | DIPE wt % | Water wt % | Gas wt % |
|---|---|---|---|---|---|---|---|---|---|---|
| 6013-500 | 9+ | 239 | 261 | 100.0 | 0.0 | 0.0 | 82.9 | 12.2 | 4.9 | 0.0 |
| 6013-600 | 14+ | 239 | 275 | 94.7 | 0.3 | 0.5 | 64.1 | 25.2 | 4.6 | 5.3 |
| 6013-700 | 22* | 303 | 258 | 100.0 | 0.0 | 0.0 | 90.4 | 4.7 | 4.9 | 0.0 |
| 6013-800 | 30* | 304 | 273 | 96.0 | 0.3 | 0.5 | 74.3 | 16.2 | 4.7 | 4.0 |

*LHSV = 2;
+ LHSV = 1

EXAMPLE 7

Example 7 is an example of the invention. The catalyst from Example 1 was loaded in the top reactor and the catalyst from Example 4 was loaded in the bottom reactor. The Catalyst Evaluation Procedure described above was used. The results for this example are given in Table III. This example illustrates that optimum yields of DIPE can be attained by adjusting the zeolite content and etherification reactor temperature. DIPE yields of up to 35.8% were achieved by using the catalyst containing 60% β-zeolite and reaction temperature about 295° F. Etherification temperature greater than 295° F. causes a deleterious effect on the combined IPA and DIPE yield because it favors the formation of undesired gas product.

The results from Examples 5, 6 and 7 clearly demonstrate that a high yield of IPA and DIPE can be generated from an integrated process where acetone is hydrogenated over a alumina supported Ni/Cu hydrogenation catalyst and the resulting IPA is dehydrated to ether over an acidic catalyst consisting of a β-zeolite/alumina support with or without additional hydrogenation function.

What is claimed:

1. An integrated process for the generation of diisopropyl ether from a crude by-product acetone stream comprising about 20% to 80% acetone which comprises:
   a) Hydrogenating said crude acetone over a supported, hydrogenation catalyst to give an isopropanol-rich effluent;
   b) passing said isopropanol without separation of liquid and gas directly to a second reactor and therein reacting said isopropanol in the presence of a strong acid zeolite catalyst from the group consisting of β-zeolite and dealuminized Y-zeolite, optionally mixed with a binder selected from Group III or IV, and optionally modified with one or more metals from Groups IB and VIII of the Periodic Table, wherein the process also provides methyl tertiary butyl ether (MTBE) and isopropyl tertiary butyl ether (IPTBE) when the by-product feed stream contains methanol and t-butanol.

2. The process of claim 1 wherein the supported hydrogenation catalyst comprises 16–28 wt % nickel and 5–16 wt % Cu on a support selected from Group III or IV.

3. The process of claim 1 wherein the β-zeolite has a silica:alumina molar ratio of at least 10:1.

4. The process of claim 1 wherein the β-zeolite has a silica:alumina molar ratio in the range of 10:1 to 50:1.

5. The process of claim 1 wherein the β-zeolite has a surface area, after calcination, at least 100 m²/g.

6. The process of claim 1 wherein the β-zeolite is characterized by the following X-ray diffraction, pattern:
   11.40±0.2
   7.40±0.2
   6.70±0.2

TABLE III

Results of Catalyst Evaluations

Example 7: Top Bed - 32% Ni/Cu on Al2O3
Bot. Bed - 32% 60/40 Beta/Al2O3

GC Analysis of Liquid Product

| Cut No. | TOS hr. | Avg. Top Temp. °F. | Avg. Bot. Temp. °F. | Liq. Recov. wt % | C3 wt % | Acetone wt % | IPA wt % | DIPE wt % | Water wt % | Gas wt % |
|---|---|---|---|---|---|---|---|---|---|---|
| 6013-500 | 5 | 241 | 242 | 100.0 | 0.0 | 0.0 | 90.5 | 4.6 | 4.9 | 0.0 |
| 6013-600 | 9 | 242 | 275 | 95.8 | 0.3 | 0.0 | 66.1 | 24.7 | 4.7 | 4.2 |
| 6013-700 | 17 | 245 | 295 | 90.8 | 0.3 | 0.0 | 50.3 | 35.8 | 4.5 | 9.2 |
| 6013-800 | 19 | 246 | 297 | 81.1 | 0.8 | 0.0 | 43.1 | 33.2 | 4.0 | 18.9 |

4.25±0.1
3.97±0.1
3.00±0.1
2.20±0.1.

7. The process of claim 1 wherein the β-zeolite catalyst is formed in the presence of a binder selected from a Group III oxide or a Group IV oxide.

8. The process of claim 7 wherein the Group III oxide binder is alumina.

9. The process of claim 8 wherein the alumina comprises 10% to 90% of the formed catalyst.

10. The process of claim 1 wherein the β-zeolite is modified with one or more metals from Groups IB and VIII of the Periodic Table.

11. The process of claim 10 wherein the β-zeolite is modified with one or more metals selected from the group consisting of copper, nickel, palladium and platinum.

12. The process of claim 10 wherein the concentrations of metals deposited on said zeolite may vary from 0.01% to 10.0% for each metal.

13. The process of claim 1 wherein the zeolite catalyst is a Y-zeolite dealuminated in a manner selected from:
   a) ammonium exchanging the Y-zeolite followed by calcinating;
   b) by treating with ethylenediaminetetraacetic acid;
   c) treating the Y-zeolite with a fluorine-containing compound from the group consisting of silicon tetrafluoride and ammonium fluorosilicate; or
   d) treating the Y-zeolite with steam alone or followed by acid treatment.

14. The process of claim 13 wherein the dealuminized Y-zeolite has a silica-to-alumina molar ratio of greater than 3.

15. The process of claim 14 wherein the Y-zeolite is dealuminated and has a silica-to-alumina molar ratio in the range 7 to 50 and a unit cell size in the range 24.26 to 24.56 Å.

16. The process of claim 1 wherein in the first stage the acetone is hydrogenated in the temperature range 120°–180° C.

17. The process of claim 1 wherein the second stage generation of diisopropyl ether, methyl tertiary butyl ether and isopropyl tertiary butyl ether is conducted in the temperature range 80° to 200° C.

18. The process of claim 1 wherein said acetone stream also contains significant quantities of both methanol and t-butanol and methyl t-butyl ether and isopropyl tertiary butyl ether are also produced.

19. The process of claim 18 wherein the methanol and t-butanol contents of the acetone by-product stream are in the range 10% to 40%.

20. An integrated process for the cogeneration of diisopropyl ether, and methyl tertiary butyl ether and isopropyl tertiary butyl ether from a crude acetone stream, also containing methanol and t-butanol, which comprises:
   a) Hydrogenating said crude acetone over a catalyst consisting essentially of nickel and copper on an alumina support to give an isopropanol-rich effluent;
   b) passing said isopropanol directly into a second reactor without separation of liquid and gas,
   c) reacting said isopropanol in the presence of hydrogen and a strong acid zeolite catalyst from the group consisting essentially of 70–90 wt % β-zeolite mixed with 10–30 wt % alumina having 0.1 to 5.0 wt % each of copper and nickel deposited thereon.

* * * * *